US008871185B2

(12) United States Patent
Blin et al.

(10) Patent No.: US 8,871,185 B2
(45) Date of Patent: Oct. 28, 2014

(54) LIP MAKEUP COMPOSITION WITH GOOD STAYING POWER COMPRISING A LOW MOLECULAR WEIGHT RESIN

(75) Inventors: Xavier Blin, Paris (FR); Shaoxiang Lu, Plainsboro, NJ (US); Hy Si Bui, Piscataway, NJ (US)

(73) Assignee: L'Oreal, Paris (FR)

( * ) Notice: Subject to any disclaimer, the term of this patent is extended or adjusted under 35 U.S.C. 154(b) by 1646 days.

(21) Appl. No.: 11/485,347

(22) Filed: Jul. 13, 2006

(65) Prior Publication Data

US 2007/0041920 A1 Feb. 22, 2007

Related U.S. Application Data

(60) Provisional application No. 60/698,790, filed on Jul. 13, 2005.

(51) Int. Cl.
*A61K 8/81* (2006.01)
*A61Q 1/06* (2006.01)
*A61K 8/97* (2006.01)

(52) U.S. Cl.
CPC ... *A61Q 1/06* (2013.01); *A61K 8/97* (2013.01); *A61K 8/8111* (2013.01); *A61K 8/8117* (2013.01)
USPC .......................................................... 424/64

(58) Field of Classification Search
USPC .......................................................... 424/64
See application file for complete search history.

(56) References Cited

U.S. PATENT DOCUMENTS

| 4,887,622 | A | 12/1989 | Gueret |
| 5,874,069 | A | 2/1999 | Mendolia et al. |
| 5,919,441 | A | 7/1999 | Mendolia et al. |
| 5,981,680 | A | 11/1999 | Petroff et al. |
| 5,989,570 | A * | 11/1999 | Lion et al. .............. 424/401 |
| 6,051,216 | A | 4/2000 | Barr et al. |
| 6,180,123 | B1 * | 1/2001 | Mondet .................. 424/401 |
| 6,328,495 | B1 | 12/2001 | Gueret |
| 6,372,235 | B1 | 4/2002 | Livoreil et al. |
| 6,386,781 | B1 | 5/2002 | Gueret |
| 6,423,306 | B2 * | 7/2002 | Caes et al. ............... 424/78.02 |
| 6,517,818 | B1 * | 2/2003 | Golz-Berner et al. ......... 424/64 |
| 6,581,610 | B1 | 6/2003 | Gueret |
| 6,649,173 | B1 | 11/2003 | Arnaud et al. |
| 6,692,173 | B2 | 2/2004 | Gueret |
| 6,866,046 | B2 | 3/2005 | Gueret |
| 6,878,378 | B1 * | 4/2005 | Yamaki et al. ............ 424/401 |
| 7,611,726 | B2 * | 11/2009 | Yu ........................... 424/401 |
| 2002/0020424 | A1 | 2/2002 | Gueret |
| 2002/0054783 | A1 | 5/2002 | Gueret |
| 2004/0258721 | A1 * | 12/2004 | Bauer et al. .............. 424/401 |
| 2005/0172421 | A1 | 8/2005 | Jager-Lezer et al. |
| 2009/0010868 | A1 * | 1/2009 | Ilekti et al. .............. 424/78.02 |

FOREIGN PATENT DOCUMENTS

| EP | 0 847 752 | B1 | 6/1998 |
| EP | 1 068 854 | B1 | 1/2001 |
| EP | 1 086 945 | B1 | 3/2001 |
| EP | 1 396 259 | A2 | 3/2004 |
| FR | 2 761 959 | A1 | 10/1998 |
| FR | 2 792 618 | A1 | 10/2000 |
| FR | 2 796 529 | A1 | 1/2001 |

OTHER PUBLICATIONS

Creton, Costantino and Hooker, Jacob. "Bulk and Interfacial Contributions to the Debonding Mechanisms of Soft Adhesives: Extension to Large Strains", Langmuir, 2001, 17, 4948-4954. Published on the web, Jul. 6, 2001.*
"Handbook of Pressure Sensitive Adhesive Technology," Second Edition, Van Nostrand Reinhold, pp. 608-619 (1989).
P. Terech, "Low-molecular weight organogelators," Specialist Surfactants, Blackie Academic & Professional, pp. 208-268 (1997).
English language Derwent Abstract of EP 1 086 945 B1, Mar. 28, 2001.
Office Action issued May 28, 2013, in Japanese Patent Application No. 2006-192103 (English-language translation only).

* cited by examiner

*Primary Examiner* — Audrea Buckley
(74) *Attorney, Agent, or Firm* — Oblon, Spivak, McClelland, Maier & Neustadt, L.L.P.

(57) ABSTRACT

The present disclosure relates to a lip makeup composition comprising at least one resin chosen from rosins, rosin derivatives and hydrocarbon-based resins, and mixtures thereof, wherein the at least one resin has a number-average molecular mass of less than or equal to 10,000 g/mol, and wherein the lip makeup composition is capable of forming a film with a resistance to oil of greater than or equal to 50%.

27 Claims, No Drawings

LIP MAKEUP COMPOSITION WITH GOOD STAYING POWER COMPRISING A LOW MOLECULAR WEIGHT RESIN

This application claims benefit of U.S. Provisional Application No. 60/698,790, filed Jul. 13, 2005, the contents of which are incorporated herein by reference.

The present disclosure relates to a composition and a process for making up the lips.

Color-fastness is an important property of makeup products. However, the properties of color-fastness and transfer resistance are generally in conflict with that of gloss. Specifically, in order to obtain fastness and transfer resistance, use is often made of compositions comprising volatile materials, for example of polymers present in these compositions comprising a volatile solvent or oil. However, these compositions may not be glossy due to the presence of volatile solvent or oil.

Thus, it has been envisioned to produce formulations in two parts, making it possible to improve the gloss and the comfort of the composition by applying a greasy glossy top coat over a colored film-forming composition. However, the top coat is usually lost in the course of the day, and although the staying power of the makeup in terms of color remains good, the disappearance of the top coat typically destroys the gloss originating therefrom. Thus the benefit of conserving the colored makeup was often largely degraded as a result of this loss of gloss.

Surprisingly and unexpectedly, the present inventors have discovered that the incorporation of a particular resin into a composition makes it possible to obtain good resistance properties, for instance with respect to resistance to oil, without harming the gloss.

Thus, proposed herein is another route for formulating a lip makeup composition that has good resistance properties, and which solves all or some of the problems associated with the conventional formulation routes.

One aspect of the present disclosure is, more specifically, a cosmetic lip makeup composition comprising at least one resin chosen from rosin, rosin derivatives and hydrocarbon-based resins, where the at least one resin has a number-average molecular mass of less than or equal to 10,000 g/mol. One benefit of the composition as disclosed herein is that it is capable of forming a film that has a resistance to oil of greater than or equal to 50%.

For instance, the composition as disclosed herein is capable of forming a film that has a deposit with a resistance to oil greater than or equal to 50%, for example 55%, 60% or even 65%.

The resistance to oil may be measured according to the following method.

Three glass slides are prepared, each covered with a sheet of collagen as follows.

A sheet of collagen (naturin artificial gut, thickness 0.06 mm, a. 0.10 mm, d. 120 mm) with a side length of 5 cm by 10 cm is prepared at a temperature of 28° C., and is conditioned for at least two hours at 90% relative humidity (RH).

The sheet of collagen is returned to the open air and is immediately attached securely and entirely to a 4.6 cm by 7.6 cm glass slide. The sheet of collagen is attached to the reverse of the glass slide with 3M Scotch tape. The surface of the collagen should be flat and free of folds. Each slide is left under ambient conditions for 24 hours before performing the test.

A 5 cm by 10 cm rectangle is cut out of a Styrofoam plate (Amoco Selectables Plastics DL Tableware type) using a knife and a ruler by following the contour of a glass slide. The composition according to the present disclosure is applied to each glass slide and to the Styrofoam rectangle as follows, using a 25 μm mechanical applicator (bar coater).

The plates are left under ambient conditions for 24 hours. Three drops of olive oil (about 0.075 g) spread out with a brush are applied to each of the three slides covered with collagen and with the composition as disclosed herein. The excess is dried up using a Kimwipes paper towel and the slides are left for 30 minutes at room temperature. Three white Styrofoam discs 4 cm in diameter are cut out.

The white Styrofoam disc is securely attached with double-sided tape to the end of a 2 kg mass, and, by exerting a pressure of 175 g/cm$^2$, the weight is gently placed on the surface of a plate (product side) and the weight is rotated one and a half times about itself over 3 to 5 seconds, while maintaining the initial pressure. The weight is raised and the Styrofoam disc is recovered. The measurement is performed for each glass slide with a clean Styrofoam disc.

The percentage of reflectance is then measured:
of the deposit of product applied to the rectangular Styrofoam sample (reference A),
of the clean white Styrofoam disc (reference B), and
of the disc detached from the weight after the pressure has been applied to the slide coated with cosmetic product (reference C).

The reflectance is measured over a wavelength ranging from 400 to 700 nm using a spectral analyser (aperture 25 mm in diameter) with a D65/10° illuminant. The wavelength of the reflectance minimum is chosen for the "stained" disc. At this wavelength, the resistance is calculated according to the equation:

$$100*(1-[(C-B)/(A-B)])$$

The resistance to oil is equal to the mean of the three measurements.

In addition, a deposit of the composition according to the present disclosure may have high gloss, for instance.

The gloss of a deposit of the composition according to the present disclosure may be measured according to the method described below.

As disclosed herein, for instance, the product according to the present disclosure may have a gloss of greater than or equal to 5, for example greater than or equal to 10, such as greater than or equal to 15, and further for example, greater than or equal to 20, such as greater than or equal to 25, or even of about 30.

The term "gloss" is generally understood to mean the gloss as may be measured by the following method, using apparatus of gonioreflectometer type, for instance the GRM-2000 machine sold by the company Micromodules.

The parameters adopted for this apparatus are as follows:
illumination angle: 120°
detection angle: 60°
start angle: 50°
end angle: 95°

A support of rectangular foam type 40×70 mm in size is made using a brick-red foam, for example a neoprene foam 3 mm thick with an adhesive face, for example a foam known under the trade reference RE40×70 EP3 sold by the company Joint Technique Lyonnais Ind.

A transparent adhesive plaster sold by the company 3M® under the trade reference Blenderm® FH 5000-55113, having a wear quality such that the application of a lipstick to this coating is similar to that produced on the lips, is attached to the face opposite the adhesive face of this support.

The foam support bearing the transparent adhesive plaster is then attached, bonding by means of its adhesive face, to a metal plate 40×70 mm in size. The assembly comprises the support bonded to the metal plate, forming a specimen.

The operator produces a total of 5 specimens identical to the one described above.

One embodiment of the process for evaluating the gloss will now be described.

The operator places the specimen on a hotplate set at a temperature of 38.5° C., for example a hotplate of the type N81076 sold by the company Fisher Bioblock, and waits for the face of the support bearing the adhesive coating to reach a temperature of 33±1° C.

Once the support is at the desired temperature, the operator applies a film about 15 μm thick of the composition.

The composition, which is, for example, a lipstick, was stored at 24±2° C.

The action performed by the operator to deposit the film of product comprises a back-and-forth motion, so as to obtain a uniform deposit. For instance, the application of the composition to the support is performed so as to be as representative as possible of the real conditions of application of the product. The same test product is applied in an identical manner to the five same specimens prepared previously.

The film of product is left to dry, the specimen being placed on the hotplate, such that the support remains at 33±1° C. for 10 minutes.

The gloss of the film of product is measured for each of the five specimens.

From the measured values, the mean gloss is established according to the following conventions:

$$\overline{Gloss} = \frac{1}{N} \sum_i Gloss_i$$

standard deviation:

$$\sigma_{Gloss} = \sqrt{\frac{N \sum_i Gloss_i^2 - \left(\sum_i Gloss_i\right)^2}{N(N-1)}}$$

95% confidence interval:

$$\overline{Gloss} \pm 1.96 \sqrt{\frac{\sigma_{Gloss}}{N}}$$

where N is the number of measurements, i.e. 5 in the present case.

Another aspect of the present disclosure involves the use of at least one resin chosen from rosin, rosin derivatives, and hydrocarbon-based resins, the at least one resin having a number-average molecular mass of less than or equal to 10,000 g/mol, in a lip makeup composition. The composition is capable of forming a film with a resistance to oil of greater than or equal to 50%.

Another aspect of the present disclosure relates to a process for making up the lips, in which a composition as defined above is applied to the lips.

The expression "at least one" is generally understood to mean one or more individual compounds, and also mixtures thereof.

The composition according to the present disclosure comprises a physiologically acceptable medium, for example a cosmetically acceptable medium, i.e. a medium that is compatible with keratin fibers such as the hair, the eyelashes or the eyebrows.

Resin

The resin used in the composition according to the present disclosure for instance has a number-average molecular mass of less than or equal to 10,000 g/mol, such as ranging from 250 to 10,000 g/mol, and for example, less than or equal to 5,000 g/mol, such as ranging from 250 to 5,000 g/mol, and further, for example, less than or equal to 2,000 g/mol, such as ranging from 250 to 2,000 g/mol and further still, for example, less than or equal to 1,000 g/mol, such as ranging from 250 to 1,000 g/mol.

The number-average molar masses (Mn) are determined by gel permeation liquid chromatography (THF solvent, calibration curve established with linear polystyrene standards, refractometric detector).

In at least one embodiment, the resin of the composition according to the present disclosure is a tackifying resin. Such resins are described, for instance, in the Handbook of Pressure Sensitive Adhesive, edited by Donatas Satas, 3rd edition, 1989, pp. 609-619.

The resin of the composition according to the present disclosure may be chosen from rosin or a derivative thereof and hydrocarbon-based resins, and mixtures thereof.

For purposes of the present disclosure, the term "hydrocarbon-based" means a compound predominantly comprising carbon and hydrogen, and possibly heteroatoms such as oxygen, nitrogen or sulfur. For example, the hydrocarbon-based compound may comprise carbon and hydrogen.

The rosin is a mixture predominantly comprising organic acids known as rosin acids (mainly acids of abietic type and of pimaric type). Three types of rosin exist: the rosin ("gum rosin") obtained by incision on live trees; wood rosin, which is extracted from pine wood or stumps; and tall oil ("tall oil rosin"), which is obtained from a by-product originating from the production of paper.

The rosin derivatives may be derived, for instance, from the polymerization, hydrogenation and/or esterification (for example with polyhydric alcohols such as ethylene glycol, glycerol or pentaerythritol) of rosin acids. Examples that may be mentioned include but are not limited to the rosin esters sold under the names FORAL 85, PENTALYN H and STAY-BELITE ESTER 10 by the company Hercules; SYLVATAC 95 and ZONESTER 85 by the company Arizona Chemical, or UNIREZ 3013 by the company Union Camp.

The hydrocarbon-based resins may be chosen from olefinic polymers of low molecular mass, which may be classified, according to the type of monomer they comprise, as indene polymers, pentadiene resins, cyclopentadiene dimer resins and terpenic resins.

The indene polymers may be chosen from polymers derived from the polymerization in major proportion of indene monomer and in minor proportion of monomers chosen from styrene, methylindene and methylstyrene, and mixtures thereof. These polymers may optionally be hydrogenated, and may have a molecular weight ranging from 200 to 1,500 g/mol.

According to at least one embodiment, the indene hydrocarbon-based polymer is a block copolymer obtained from indene and from styrene or a styrene derivative.

According to at least one embodiment, the resin is chosen from indene resins, such as the hydrogenated indene/methylstyrene/styrene copolymers sold under the name "Regalite" by the company Eastman Chemical, such as REGALITE R 1100, REGALITE R 1090, REGALITE R-7100, REGALITE R 1010 HYDROCARBON RESIN and REGALITE R 1125 HYDROCARBON RESIN.

By way of example, suitable indene polymers that may be mentioned include but are not limited to those sold under the name ESCOREZ 7105 by the company Exxon Chem., NEVCHEM 100 and NEVEX 100 by the company Neville Chem., NORSOLENE S105 by the company Sartomer, PICCO 6100 by the company Hercules and RESINALL by the company Resinall Corp.

Other non-limiting examples of indene polymers include pentadiene and indene resins, which are derived from the polymerization of a mixture of pentadiene and indene monomers such as those described above, for instance the resins sold under the name ESCOREZ 2101 by the company Exxon Chemicals, NEVPENE 9500 by the company Neville Chem., HERCOTAC 1148 by the company Hercules, NORSOLENE A 100 by the company Sartomer, and WINGTACK 86, WINGTACK EXTRA and WINGTACK PLUS by the company Goodyear.

The pentadiene resins may be chosen from those derived from the polymerization in major proportion of the 1,3-pentadiene (trans or cis-piperylene) monomer and of minor monomers chosen from isoprene, butene, 2-methyl-2-butene, pentene and 1,4-pentadiene, and mixtures thereof. These resins may have a molecular weight ranging from 1,000 to 2,500 g/mol.

Such 1,3-pentadiene resins are sold, for example, under the names PICCOTAC 95 by the company Eastman Chemical, ESCOREZ 1304 by the company Exxon Chemicals, NEVTAC 100 by the company Neville Chem. or WING-TACK 95 by the company Goodyear.

The cyclopentadiene dimer resins may be chosen from those derived from the polymerization of first monomers chosen from indene and styrene, and of second monomers chosen from cyclopentadiene dimers such as dicyclopentadiene, methyldicyclopentadiene and other pentadiene dimers, and mixtures thereof. These resins generally have a molecular weight ranging from 500 to 800 g/mol, for instance those sold under the reference BETAPRENE BR 100 by the company Arizona Chemical Co., NEVILLE LX-685-125 and NEVILLE LX-1000 by the company Neville Chem., PICCODIENE 2215 by the company Hercules, PETRO-REZ 200 by the company Lawter or RESINALL 760 by the company Resinall Corp.

The terpenic resins may be chosen from those derived from the polymerization of at least one monomer chosen from α-pinene, β-pinene and limonene, and mixtures thereof. These resins may have a molecular weight ranging from 300 to 2,000 g/mol. Such resins are sold, for example, under the names PICCOLYTE A115 and S125 by the company Hercules, and ZONAREZ 7100 or ZONATAC 105 LITE by the company Arizona Chem.

Hydrocarbon-based resins that may also be mentioned include but are not limited to certain resins sold under the name EASTOTAC C6-C20 Polyolefin by the company Eastman Chemical Co., under the name ESCOREZ 5300 by the company Exxon Chemicals, or the resins NEVILLAC HARD or NEVROZ Sold by the company Neville Chem., the resins PICCOFYN A-100, PICCOTEX 100 or PICCOVAR AP 25 sold by the company Hercules or the resin SP-553 sold by the company Schenectady Chemical Co.

One aspect of the present disclosure is a cosmetic lip makeup composition comprising at least one indene hydrocarbon-based polymer with a number-average molecular mass of less than or equal to 10,000 g/mol. One benefit of the composition is its capability to form a film with a resistance to oil of greater than or equal to 50%. For example, according to at least one embodiment, the indene polymer may be one of the indene polymers that was described previously. According to at least one embodiment, the indene hydrocarbon-based polymer is a block copolymer obtained from indene and from styrene or a styrene derivative.

The resin may be present in the composition according to the present disclosure in an amount ranging from 0.1% to 40% by weight, for example ranging from 0.5% to 30% by weight, for instance ranging from 1% to 20% by weight, and further, for example from 2% to 15% by weight, relative to the total weight of the composition.

The resin may have at least one glass transition temperature, for instance greater than or equal to 20° C., for example greater than or equal to 30° C., such as about 40° C. For instance, the glass transition temperature may range from 20° C. to 300° C., for example ranging from 30° C. to 100° C.

The glass transition temperatures indicated herein may be theoretical Tg values, as determined from the theoretical Tg values of the constituent monomers of each of the blocks, which may be found in a reference manual such as the Polymer Handbook, 3rd edition, 1989, John Wiley, according to the following relationship, known as Fox's law:

$$1/Tg = \sum_i (\overline{\omega}_i / Tg_i),$$

$\overline{\omega}_i$ being the mass fraction of the monomer i in the block under consideration and $Tg_i$ being the glass transition temperature of the homopolymer of the monomer i.

The glass transition temperature (Tg) may be measured according to standard ASTM D3418-97, via differential thermal analysis (DSC, "Differential Scanning Calorimetry") on a calorimeter, over a temperature range from −100° C. to +150° C. at a heating rate of 10° C./minute in 150 μl aluminium crucibles.

Liquid Fatty Phase

The composition according to the present disclosure may comprise a fatty phase that is liquid at room temperature (25° C.) and atmospheric pressure (760 mmHg), composed of at least one mutually compatible non-aqueous fatty substance that is liquid at room temperature, also known as an organic solvent or oil.

The oil may be chosen from volatile oils and/or non-volatile oils, and mixtures thereof.

For the purposes of the present disclosure, the term "volatile oil" means an oil that is capable of evaporating on contact with the skin or the keratin fiber in less than one hour, at room temperature and atmospheric pressure. The volatile organic solvent(s) and volatile oils of the present disclosure are volatile organic solvents and cosmetic oils that are liquid at room temperature, with a non-zero vapor pressure at room temperature and atmospheric pressure, for instance ranging from 0.13 Pa to 40,000 Pa ($10^{-3}$ to 300 mmHg), for example ranging from 1.3 Pa to 13,000 Pa (0.01 to 100 mmHg), and further, for example ranging from 1.3 Pa to 1,300 Pa (0.01 to 10 mmHg). The term "non-volatile oil" means an oil that remains on the skin or the keratin fiber at room temperature and atmospheric pressure for at least several hours and has a vapor pressure of less than $10^{-3}$ mmHg (0.13 Pa), for instance.

These oils may be hydrocarbon-based oils, silicone oils or fluoro oils, or mixtures thereof.

The term "hydrocarbon-based oil" means an oil mainly comprising hydrogen and carbon atoms and optionally oxygen, nitrogen, sulfur or phosphorus atoms. The volatile hydrocarbon-based oils may be chosen from hydrocarbon-based oils containing from 8 to 16 carbon atoms, for example branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane and isohexadecane, for example the oils sold under the trade names Isopar or Permethyl, branched $C_8$-$C_{16}$ esters and isohexyl neopentanoate, and mixtures thereof. Other suitable volatile hydrocarbon-based oils include, for instance, petroleum distillates, such as those sold under the name SHELL SOLT by the company Shell. The volatile solvent may be chosen, for instance, from volatile hydrocarbon-based oils comprising from 8 to 16 carbon atoms, and mixtures thereof.

Volatile oils that may also be used include volatile silicones, for instance volatile linear or cyclic silicone oils, such as those with a viscosity ≤8 centistokes ($8 \times 10^{-6}$ m$^2$/s) and further, for example, those comprising from 2 to 7 silicon atoms, these silicones optionally comprising alkyl or alkoxy groups comprising from 1 to 10 carbon atoms. As disclosed herein, volatile silicone oils that may be used include but are not limited to, for example: octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyl tetrasiloxane and dodecamethylpentasiloxane, and mixtures thereof.

Non-limiting mention may also be made of the linear volatile alkyltrisiloxane oils of formula (I):

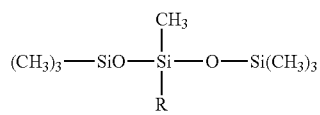

in which R is an alkyl group containing from 2 to 4 carbon atoms and where at least one of the hydrogen atoms may be substituted with at least one fluorine or chlorine atoms.

As disclosed herein, oils of formula (I) that may be mentioned include but are not limited to:
3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane,
corresponding to the oils of formula (I) for which R is, respectively, a butyl group, a propyl group or an ethyl group.

Volatile fluorinated solvents such as nonafluoromethoxybutane or perfluoromethylcyclopentane may also be used.

The composition may also comprise at least one non-volatile oil, chosen for example from non-volatile hydrocarbon-based oils and/or silicone oils and/or fluoro oils.

Non-volatile hydrocarbon-based oils that may be mentioned include, for example:
hydrocarbon-based oils of plant origin, such as triesters of fatty acids and of glycerol, the fatty acids of which may have varied chain lengths from $C_4$ to $C_{24}$, these chains possibly being linear or branched, and saturated or unsaturated; these oils including but not limited to wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppyseed oil, pumpkin oil, marrow oil, blackcurrant oil, evening primrose oil, millet oil, barley oil, quinoa oil, rye oil, safflower oil, candlenut oil, passionflower oil and musk rose oil; and caprylic/capric acid triglycerides, for instance those sold by the company Stéarineries Dubois or those sold under the names MIGLYOL 810, 812 and 818 by the company Dynamit Nobel,
synthetic ethers containing from 10 to 40 carbon atoms,
linear or branched hydrocarbons of mineral or synthetic origin, such as petroleum jelly, polydecenes, hydrogenated polyisobutene such as parleam, and squalane, and mixtures thereof,
fatty alcohols that are liquid at room temperature with a branched and/or unsaturated $C_{12}$ to $C_{26}$ carbon-based chain, for instance octyldodecanol, isostearyl alcohol, oleyl alcohol, 2-hexyldecanol, 2-butyloctanol or 2-undecylpentadecanol,
higher fatty acids such as oleic acid, linoleic acid or linolenic acid,
and mixtures thereof.

According to at least one embodiment of the present disclosure, the composition contains a polar oil, for example an alcohol chosen from fatty alcohols that are liquid at room temperature, with a branched and/or unsaturated $C_{12}$ to $C_{26}$ carbon-based chain, for instance octyldodecanol, isostearyl alcohol, oleyl alcohol, 2-hexyldecanol, 2-butyloctanol and 2-undecylpentadecanol.

The non-volatile silicone oils that may be used in the composition according to the present disclosure may be non-volatile polydimethylsiloxanes (PDMS), polydimethylsiloxanes comprising alkyl or alkoxy groups, which are pendent and/or at the end of a silicone chain, these groups each contain from 2 to 24 carbon atoms, phenyl silicones, for instance phenyl trimethicones, phenyl dimethicones, phenyltrimethyl siloxydiphenylsiloxanes, diphenyl dimethicones, diphenyl methyidiphenyl trisiloxanes and 2-phenylethyl trimethyl siloxy silicates.

The fluoro oils that may be used in the present disclosure include, for example, fluorosilicone oils, fluoro polyethers and fluorosilicones as described in document EP-A-847 752.

According to at least one embodiment, the fatty phase contains an ester oil. This ester oil may be chosen from the esters of monocarboxylic acids with monoalcohols and polyalcohols.

For instance, the said ester corresponds to formula (II) below:

where $R_1$ is a linear or branched alkyl radical of 1 to 40 carbon atoms, such as 7 to 19 carbon atoms, optionally comprising at least one ethylenic double bond, and optionally substituted,
$R_2$ is a linear or branched alkyl radical of 1 to 40 carbon atoms, such as 3 to 30 carbon atoms, or 3 to 20 carbon atoms, optionally comprising at least one ethylenic double bond, and optionally substituted.

The term "optionally substituted" means that $R_1$ and/or $R_2$ can bear at least one substituent chosen, for example, from groups comprising at least one heteroatoms chosen from O, N and S, such as amino, amine, alkoxy and hydroxyl.

In at least one embodiment, the total number of carbon atoms of $R_1+R_2$ is ≥9.

$R_1$ may represent the residue of a linear or branched fatty acid, for example a higher fatty acid, comprising from 1 to 40, such as from 7 to 19 carbon atoms, and $R_2$ may represent a linear or branched hydrocarbon-based chain comprising from 1 to 40, for example from 3 to 30 or from 3 to 20 carbon atoms. In at least one embodiment, $R_1$ represents the residue of a branched fatty acid and/or $R_2$ represents a branched hydrocarbon-based chain. As stated above, in at least one embodiment, the number of carbon atoms of $R_1+R_2 \geq 9$.

Examples of groups $R_1$ are those derived from fatty acids chosen from the group comprising of acetic acid, propionic acid, butyric acid, caproic acid, caprylic acid, pelargonic acid, capric acid, undecanoic acid, lauric acid, myristic acid, palmitic acid, stearic acid, isostearic acid, arachidic acid, behenic acid, oleic acid, linolenic acid, linoleic acid, oleostearic acid, arachidonic acid and erucic acid, and mixtures thereof.

Non-limiting examples of esters include but are not limited to purcellin oil (cetostearyl octanoate), isononyl isononanoate, isopropyl myristate, 2-ethylhexyl palmitate, 2-octyldodecyl stearate, 2-octyldodecyl erucate, isostearyl isostearate, and heptanoates, octanoates, decanoates or ricinoleates of alcohols or polyalcohols, for example of fatty alcohols.

For instance, the esters may be chosen from the compounds of formula (I) above, in which $R_1$ is an unsubstituted linear or branched $C_1$ to $C_{40}$ alkyl group, such as $C_7$ to $C_{19}$ carbon atoms, optionally comprising at least one ethylenic double bond, and $R_2$ is an unsubstituted linear or branched $C_1$ to $C_{40}$ alkyl group, such as $C_3$ to $C_{30}$, optionally comprising at least one ethylenic double bond.

According to at least one embodiment, $R_1$ is an unsubstituted branched alkyl group of 4 to 14 carbon atoms, such as 8 to 10 carbon atoms, and $R_2$ is an unsubstituted branched alkyl group of 5 to 15 carbon atoms, such as 9 to 11 carbon atoms. For instance, according to at least one embodiment, in formula (I), $R_1$—CO— and $R_2$ have the same number of carbon atoms and are derived from the same radical, for instance an unsubstituted branched alkyl, for example isononyl, i.e. the ester oil molecule is beneficially symmetrical.

For instance, the ester oil may be chosen from the following compounds:
isononyl isononanoate,
cetostearyl octanoate,
isopropyl myristate,
2-ethylhexyl palmitate,
2-octyldodecyl stearate,
2-octyldodecyl erucate,
isostearyl isostearate.

The liquid fatty phase may be present in an amount ranging from 0.5% to 90% by weight, for instance ranging from 1% to 60% and further ranging from 2% to 40% by weight relative to the total weight of the composition.

Hydrocarbon-Based Block Copolymer

According to at least one embodiment of the present disclosure, the composition comprises, besides the resin, at least one hydrocarbon-based block copolymer also known as at least one block copolymer, including, for example a block copolymer that is soluble in a liquid fatty phase as defined above.

For instance, as disclosed herein, the copolymer may comprise at least one block copolymer with a glass transition temperature of less than 20° C., such as less than or equal to 0° C., for example less than or equal to −20° C. and further still, for example, less than or equal to −40° C. The glass transition temperature of the at least one block copolymer may range from −150° C. to 20° C., such as from −100° C. to 0° C.

In this case, when the resin has at least one glass transition temperature, the difference between the glass transition temperatures of the resin and of the copolymer is generally greater than 20° C., such as greater than 40° C. and further still greater than 60° C. When the resin has at least one glass transition temperature, the at least one block copolymer is, for instance, a plasticizer for the resin described previously. The term "resin plasticizer" is generally understood to mean a compound which, when combined in sufficient amount with the resin, lowers the glass transition temperature of the resin as defined previously. For instance, the plasticizer compound lowers the glass transition temperature of the polymer by at least 2, 3 or 4° C., such as from 5° C. to 20° C. According to at least one embodiment, the plasticizer compound lowers the glass transition temperature of the polymer by at least 2, 3 or 4° C., such as from 5° C. to 20° C., for example.

The at least one block copolymer may be chosen from optionally hydrogenated diblock, triblock, multiblock or radial block copolymers, and mixtures thereof.

In at least one embodiment, the at least one block copolymer may comprise at least one styrene block and at least one block comprising units chosen from butadiene, ethylene, propylene, butylene and isoprene or a mixture thereof.

Diblock copolymers that may be mentioned include but are not limited to styrene/ethylene-propylene copolymers (comprising a styrene block and a block obtained from ethylene and propylene), styrene/ethylene-butylene copolymers, styrene/butadiene copolymers and styrene/isoprene copolymers. For instance, such copolymers are sold under the name Kraton® G1701E by the company Kraton Polymers.

Triblock copolymers that may be mentioned include but are not limited to styrene/ethylene-propylene/styrene copolymers, styrene/ethylene-butylene/styrene copolymers, styrene/ethylene-butadiene/styrene copolymers, styrene/isoprene/styrene copolymers and styrene/butadiene/styrene copolymers. For instance, triblock polymers sold under the names Kraton® G1650, Kraton® G1652, Kraton® D1101, Kraton® D1102 and Kraton® D1160 by the company Kraton Polymers may be used.

For instance, a mixture of a diblock copolymer and of a triblock copolymer may be used as block copolymer. According to at least one embodiment, the diblock copolymer and the triblock copolymer may be chosen from block copolymers comprising at least one styrene block and at least one block comprising units chosen from butadiene, ethylene, propylene, butylene and isoprene.

For instance, the product sold under the reference Kraton G 1657 M, which is a mixture of styrene/ethylene-butylene diblock copolymer and of styrene/ethylene-butylene/styrene triblock copolymer in 30/70 proportions, the glass transition temperature of the ethylene-butylene block being equal to about −60° C. may be used.

It is also possible to use a mixture of hydrogenated styrene/butylene-ethylene/styrene triblock copolymer and of hydrogenated ethylene/propylene/styrene star polymer. Such mixtures are sold, for example, by the company Penreco under the trade names Versagel® M5960 and Versagel® M5670.

The hydrocarbon-based block copolymer may be present in an amount ranging from 0.1% to 25% by weight, such as from 0.5% to 15% by weight relative to the total weight of the composition.

The mass ratio between the hydrocarbon-based resin and the hydrocarbon-based block copolymer ranges from 80/20 to 40/60, for example from 75/25 to 50/50.

The composition may comprise an aqueous phase, which comprises water and/or at least one water-soluble solvent.

As disclosed herein, the term "water-soluble solvent" is generally understood to mean a compound that is liquid at room temperature and water-miscible (miscibility with water of greater than 50% by weight at 25° C. and atmospheric pressure).

The water-soluble solvents that may be used in the compositions according to the present disclosure may also be volatile.

Among the water-soluble solvents that may be used in the compositions according to the present disclosure, non-limiting mention may be made of lower monoalcohols containing from 1 to 5 carbon atoms, such as ethanol and isopropanol, $C_2$ to $C_8$ glycols, such as ethylene glycol, propylene glycol, 1,3-butylene glycol and dipropylene glycol, $C_3$ and $C_4$ ketones and $C_2$-$C_4$ aldehydes.

The aqueous phase (water and possibly the water-miscible solvent) may be present in an amount ranging from 5% to 95% by weight, such as ranging from 10% to 80% by weight and for example ranging from 15% to 60% by weight relative to the total weight of the composition.

The composition according to the present disclosure may contain emulsifying surfactants, for instance present in an amount ranging from 0.1% to 30% by weight, for example from 1% to 15% and further still from 2% to 10% by weight relative to the total weight of the composition.

The composition according to the present disclosure may comprise at least one agent for structuring the oily phase, chosen from:

- the semi-crystalline polymers described, for example, in European Patent EP 1 396 259;
- mineral lipophilic gelling agents, for instance optionally modified clays, for instance hectorites modified with a $C_{10}$-$C_{22}$ fatty-acid-ammonium chloride, for instance hectorite modified with distearyldimethylammonium chloride, for instance the product sold under the name Bentone 38V® by the company Elementis. Non-limiting mention may also be made of pyrogenic silica that has optionally been hydrophobically surface-treated, the particle size of which is less than 1 µm;
- molecular organo-gelling agents, for example those described in the document "Specialist Surfactants" edited by D. Robb, 1997, pp. 209-263, Chapter 8 by P. Terech, in European Patent Applications EP-A-1 068 854 and EP-A-1 086 945 or in Patent Application WO-A-02/47031;
- partially or totally crosslinked elastomeric organopolysiloxanes, of three-dimensional structure, such as those sold under the names KSG6®, KSG16® and KSG18® by the company Shin-Etsu;
- polycondensates of polyamide type comprising at least one carboxylic acid end group esterified or amidated with at least one monoalcohol or one monoamine containing from 12 to 30 linear and saturated carbon atoms, and further, for example copolymers such as the products sold under the Uniclear names by the company Arizona Chemical;
- silicone polyamides of the polyorganosiloxane type, such as those described in documents U.S. Pat. No. 5,874,069, U.S. Pat. No. 5,919,441, U.S. Pat. No. 6,051,216 and U.S. Pat. No. 5,981,680, for instance those sold under the name Dow Corning 2-8179 Gellant by the company Dow Corning;
- galactomannans comprising from one to six, such as from two to four hydroxyl groups per saccharide, substituted with a saturated or unsaturated alkyl chain, for instance guar gum alkylated with $C_1$-$C_6$, such as $C_1$-$C_3$ alkyl chains, and mixtures thereof.

The composition according to the present disclosure comprises at least one wax.

The at least one wax useful herein may be a lipophilic compound that is solid at room temperature (25° C.), with a solid/liquid reversible change of state, having a melting point of greater than or equal to 30° C., which may be up to 200° C. and further, for example up to 120° C.

By bringing the wax to the liquid form (melting), it is possible to make it miscible with oils and to form a microscopically uniform mixture, but on cooling the mixture to room temperature, recrystallization of the wax in the oils of the mixture is obtained.

For instance, the waxes that are suitable for the present disclosure may have a melting point of greater than or equal to 45° C., such as greater than or equal to 55° C.

The waxes that may be used in the compositions according to the present disclosure are chosen from waxes that are solid at room temperature of animal, plant, mineral or synthetic origin, and mixtures thereof.

As illustrations of waxes that are suitable for the present disclosure, non-limiting mention may be made of hydrocarbon-based waxes, for instance beeswax, lanolin wax, Chinese insect waxes, rice bran wax, carnauba wax, candelilla wax, ouricurry wax, esparto grass wax, berry wax, shellac wax, Japan wax and sumach wax; montan wax, orange wax and lemon wax, microcrystalline waxes, paraffins and ozokerite; polyethylene waxes, the waxes obtained by Fischer-Tropsch synthesis and waxy copolymers, and also esters thereof.

Non-limiting mention may also be made of waxes obtained by catalytic hydrogenation of animal or plant oils containing linear or branched $C_8$-$C_{32}$ fatty chains. Among these waxes, non-limiting mention may be made of isomerized jojoba oil such as the trans-isomerized partially hydrogenated jojoba oil manufactured or sold by the company Desert Whale under the commercial name Iso-Jojoba-500, hydrogenated sunflower oil, hydrogenated castor oil, hydrogenated coconut oil, hydrogenated lanolin oil and bis(1,1,1-trimethylolpropane) tetrastearate sold under the name Hest 2T-4S® by the company Heterene.

Non-limiting mention may also be made of silicone waxes and fluoro waxes.

The composition according to the present disclosure may comprise the at least one wax in an amount ranging from 5% to 20% by weight and for example from 7% to 15% by weight, relative to the total weight of the composition.

Besides the resin, the composition may comprise a film-forming polymer. According to the present disclosure, the term "film-forming polymer" means a polymer that is capable, by itself or in the presence of an auxiliary film-forming agent, of forming a continuous film that adheres to a support, such as to keratin materials.

The composition according to the present disclosure may also comprise at least one dyestuff, for instance pulverulent dyes, liposoluble dyes and water-soluble dyes.

The pulverulent dyestuffs may be chosen from pigments and nacres.

The pigments may be white or colored, mineral and/or organic, and coated or uncoated. As disclosed herein, mineral pigments that may be mentioned include but are not limited to titanium dioxide, optionally surface-treated, zirconium oxide, zinc oxide or cerium oxide, and also iron oxide or chromium oxide, manganese violet, ultramarine blue, chromium hydrate and ferric blue. As disclosed herein, the organic pigments that may be mentioned include but are not limited to carbon black, pigments of D & C type, and lakes based on cochineal carmine or on barium, strontium, calcium and aluminium.

The nacres may be chosen from white nacreous pigments such as mica coated with titanium or with bismuth oxychloride, colored nacreous pigments such as titanium mica with iron oxides, titanium mica with, for instance ferric blue or chromium oxide, titanium mica with an organic pigment of the above-mentioned type, and also nacreous pigments based on bismuth oxychloride.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto.

These dyestuffs may be present in an amount ranging from 0.01% to 30% by weight relative to the total weight of the composition.

The composition according to the present disclosure may also comprise at least one filler.

The at least one filler may be chosen from those that are well known to persons skilled in the art and commonly used in cosmetic compositions. The fillers may be mineral or organic, and lamellar or spherical. Non-limiting mention may be made of talc, mica, silica, kaolin, polyamide powders, for instance the Nylon® sold under the trade name Orgasol® by the company Atochem, poly-β-alanine powders and polyethylene powders, powders of tetrafluoroethylene polymers, for instance Teflon®, lauroyllysine, starch, boron nitride, expanded polymeric hollow microspheres such as those of polyvinylidene chloride/acrylonitrile, for instance the products sold under the name Expancel® by the company Nobel Industrie, acrylic powders, such as those sold under the name Polytrap® by the company Dow Corning, polymethyl methacrylate particles and silicone resin microbeads (for example Tospearls® from Toshiba), precipitated calcium carbonate, magnesium carbonate and magnesium hydrocarbonate, hydroxyapatite, hollow silica microspheres (Silica Beads® from Maprecos), glass or ceramic microcapsules, metal soaps derived from organic carboxylic acids containing from 8 to 22 carbon atoms, such as from 12 to 18 carbon atoms, for example zinc, magnesium or lithium stearate, zinc laurate and magnesium myristate.

It is also possible to use a compound that is capable of swelling on heating, for instance heat-expandable particles such as non-expanded microspheres of copolymer of vinylidene chloride/acrylonitrile/methyl methacrylate or of acrylonitrile homopolymer copolymer, for instance those sold, respectively, under the references Expancel® 820 DU 40 and Expancel® 007WU by the company Akzo Nobel.

The at least one filler may be present in an amount ranging from 0.1% to 25%, such as from 1% to 20% by weight relative to the total weight of the composition.

The composition of the present disclosure may also comprise any additive typically used in cosmetics, such as antioxidants, preserving agents, fibers, fragrances, neutralizers, gelling agents, thickeners, vitamins, coalescers and plasticizers, and mixtures thereof.

As disclosed herein, cosmetic active agents that may be used in the compositions according to the present disclosure, include but are not limited to antioxidants, preserving agents, fragrances, neutralizers, emollients, moisturizers, vitamins and screening agents, such as sunscreens.

Needless to say, a person skilled in the art will take care to select the optional additional additives and/or the amount thereof such that the beneficial properties of the composition according to the present disclosure are not, or are not substantially, adversely affected by the envisaged addition.

The compositions according to the present disclosure may be prepared according to methods known to those skilled in the art.

The composition according to the present disclosure may be packaged in a container delimiting at least one compartment that comprises the composition as disclosed herein, the container being closed by a closing member.

According to at least one embodiment, the container is associated with an applicator, such as in the form of a brush comprising an arrangement of bristles maintained by a twisted wire. For instance, such a twisted brush is described in U.S. Pat. No. 4,887,622. It may also be in the form of a comb comprising a plurality of application members, obtained by molding, for instance. Such combs are described, for example, in French Patent FR 2 796 529. The applicator may be solidly attached to the container, as described, for example, in French Patent FR 2761 959. According to at least one embodiment, the applicator is solidly attached to a stem, which is itself solidly attached to the closing member.

The closing member may be coupled to the container by screwing. Alternatively, the coupling between the closing member and the container may take place in a manner other than by screwing, for instance via a bayonet mechanism, by click-fastening or by tightening. The term "click-fastening" is generally understood to mean any system involving the passing of a rim or bead of material by elastic deformation of a portion, for example the closing member, followed by return to the elastically unstressed position of the portion after the rim or bead has been passed.

The container may be at least partly made of thermoplastic material. Non-limiting examples of thermoplastic materials that may be mentioned include polypropylene and polyethylene.

Alternatively, the container may made of a non-thermoplastic material, such as of glass or metal (or alloy).

According to at least one embodiment of the present disclosure, the container is equipped with a drainer located in the region of the aperture of the container. Such a drainer makes it possible to wipe the applicator and, optionally, the stem to which it may be solidly attached. Such a drainer is described, for example, in French Patent FR 2 792 618.

The content of the patents or patent applications mentioned previously are hereby incorporated by reference into the present patent application.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in its respective testing measurement.

The example that follows is intended to illustrate the present disclosure without, however, being limiting in nature.

EXAMPLE

The lipstick according to the present disclosure was prepared as listed below, with proportions listed in grams:

| | |
|---|---|
| Hydrogenated styrene/methylstyrene/indene copolymer (REGALITE R1100 from Eastman) | 16 g |
| Hydrogenated styrene/butadiene copolymer (KRATON 1657 M)* | 10 g |
| Isododecane | qs 100 g |
| Octyldodecanol | 3.1 g |
| Pigments | 3.1 g |
| Nacres | 2 g |

*Kraton 1657 M was a mixture of diblock copolymer and triblack copolymer in 70/30 proportions comprising styrene blocks and ethylene-butylene blocks.

The resistance to oil and the gloss of the composition were measured according to the measuring methods as previously described herein.

The resistance to oil, measured according to the method described previously, was equal to 68%.

Procedure:
1. A ground pigmentary mixture of the pigments was prepared in the oily phase by grinding the mixture three times in a three-roll mill.
2. The copolymer(s) and the oil were introduced into a heating pan, and the mixture was stirred using a Rayneri blender at a temperature of 100° C.
3. When a transparent liquid mixture was observed, the ground material and the nacres were introduced, and stirring of the mixture was continued in the Rayneri blender at a temperature of 100° C. for 20 minutes.
4. A quantity sufficient for 100% was made up with the oil.
5. The formulation was poured into isododecane-leaktight jars.

What is claimed is:

1. A cosmetic lip makeup composition comprising a liquid fatty phase, at least one hydrocarbon-based block copolymer that is soluble in the liquid fatty phase, and at least one indene polymer,
wherein the at least one hydrocarbon-based block copolymer is chosen from block copolymers comprising at least one styrene block and at least one block comprising units chosen from butadiene, ethylene, propylene, butylene and isoprene, and mixtures thereof, and is present in an amount ranging from 0.1% to 25% by weight relative to the total weight of the composition,
wherein the at least one indene polymer comprises an indene monomer as the major component and at least one of styrene, methylindene and methylstyrene as the minor component and the at least one indene polymer has a number-average molecular mass of less than or equal to 10,000 g/mol, and
wherein the cosmetic lip makeup composition can form a film with a resistance to oil of greater than or equal to 50%.

2. The cosmetic lip makeup composition according to claim 1, wherein the cosmetic lip makeup composition can form a film with a resistance to oil of greater than or equal to 55%.

3. The cosmetic lip makeup composition according to claim 2, wherein the cosmetic lip makeup composition can form a film with a resistance to oil of greater than or equal to 65%.

4. The cosmetic lip makeup composition according to claim 1, wherein the at least one indene polymer has a number-average molecular mass ranging from 250 to 10,000 g/mol.

5. The cosmetic lip makeup composition according to claim 4, wherein the at least one indene polymer has a number-average molecular mass ranging from 250 to 1000 g/mol.

6. The cosmetic lip makeup composition according to claim 1, wherein the at least one indene polymer is present in an amount ranging from 0.1% to 20% by weight relative to the total weight of the composition.

7. The cosmetic lip makeup composition according to claim 6, wherein the at least one indene polymer is present in an amount ranging from 1% to 10% by weight relative to the total weight of the composition.

8. The cosmetic lip makeup composition according to claim 1, wherein the liquid fatty phase comprises at least one hydrocarbon-based volatile oil.

9. The cosmetic lip makeup composition according to claim 1, wherein the liquid fatty phase comprises a fatty alcohol.

10. The cosmetic lip makeup composition according to claim 1, wherein the liquid fatty phase represents from 0.5% to 90% by weight relative to the total weight of the composition.

11. The cosmetic lip makeup composition according to claim 10, wherein the liquid fatty phase represents from 2% to 40% by weight relative to the total weight of the composition.

12. The cosmetic lip makeup composition according to claim 1, wherein the at least one hydrocarbon-based block copolymer is present in an amount ranging from 0.5% to 15% by weight relative to the total weight of the composition.

13. The cosmetic lip makeup composition according to claim 1, wherein the at least one hydrocarbon-based block copolymer is a plasticizer for the at least one indene polymer.

14. The cosmetic lip makeup composition according to claim 1, wherein the at least one indene polymer is present with the at least one hydrocarbon-based block copolymer in a mass ratio ranging from 80/20 to 40/60.

15. The cosmetic lip makeup composition according to claim 14, wherein the at least one indene polymer and the at least one hydrocarbon-based block copolymer are present in a mass ratio ranging from 75/25 to 50/50.

16. The cosmetic lip makeup composition according to claim 1, further comprising at least one wax, at least one mineral gelling agent and/or at least one organo-gelling agent.

17. The cosmetic lip makeup composition according to claim 16, wherein the at least one wax is present in an amount ranging from 5% to 20% by weight relative to the total weight of the composition.

18. The cosmetic lip makeup composition according to claim 17, wherein the at least one wax is present in an amount ranging from 7% to 15% by weight relative to the total weight of the composition.

19. The cosmetic lip makeup composition according to claim 1, further comprising at least one dyestuff.

20. The cosmetic lip makeup composition according to claim 19, wherein the at least one dyestuff is present in an amount ranging from 0.01% to 30% by weight relative to the total weight of the composition.

21. A process for making up the lips, comprising applying a cosmetic lip composition to the lips, wherein the cosmetic lip makeup composition comprises a liquid fatty phase, at least one hydrocarbon-based block copolymer that is soluble in the liquid fatty phase, and at least one indene polymer,
wherein the at least one hydrocarbon-based block copolymer is chosen from block copolymers comprising at least one styrene block and at least one block comprising units chosen from butadiene, ethylene, propylene, butylene and isoprene, and mixtures thereof, and is present in an amount ranging from 0.1% to 25% by weight relative to the total weight of the composition,
wherein the at least one indene polymer comprises an indene monomer as the major component and at least one of styrene, methylindene and methylstyrene as the minor component and the at least one indene polymer has a number-average molecular mass of less than or equal to 10,000 g/mol,
and
wherein the cosmetic lip makeup composition can form a film with a resistance to oil of greater than or equal to 50%.

22. A method for making a lip makeup composition which can form a film with a resistance to oil of greater than or equal to 50%, said method comprising including in a lip makeup composition a liquid fatty phase, at least one hydrocarbon-based block copolymer that is soluble in the liquid fatty phase, and at least one indene polymer comprising an indene monomer as the major component and at least one of styrene, methylindene and methylstyrene as the minor component and the at least one indene polymer has a number-average molecular mass of less than or equal to 10,000 g/mol, in an amount sufficient to obtain a composition which can form a film with a resistance to oil of greater than or equal to 50% wherein the at least one hydrocarbon-based block copolymer is chosen from block copolymers comprising at least one styrene block and at least one block comprising units chosen from butadiene, ethylene, propylene, butylene and isoprene, and mixtures thereof, and is present in an amount ranging from 0.1% to 25% by weight relative to the total weight of the composition.

23. The cosmetic lip makeup composition according to claim 1, wherein the at least one hydrocarbon-based block copolymer is a triblock copolymer.

24. The cosmetic lip makeup composition according to claim 23, wherein the at least one hydrocarbon-based block copolymer is styrene/ethylene-butylene/styrene.

25. The cosmetic lip makeup composition according to claim 1, wherein the composition is liquid.

26. A cosmetic lip makeup composition comprising a liquid fatty phase, at least one hydrocarbon-based block copolymer that is soluble in the liquid fatty phase, and at least one hydrogenated indene/methylstyrene/styrene copolymer, wherein the at least one hydrocarbon-based block copolymer is chosen from block copolymers comprising at least one styrene block and at least one block comprising units chosen from butadiene, ethylene, propylene, butylene and isoprene, and mixtures thereof, and is present in an amount ranging from 0.1% to 25% by weight relative to the total weight of the composition, wherein the at least one hydrogenated indene/methylstyrene/styrene copolymer has a number-average molecular mass of less than or equal to 10,000 g/mol, and wherein the cosmetic lip makeup composition can form a film with a resistance to oil of greater than or equal to 50%.

27. The cosmetic lip makeup composition according to claim 1, wherein the indene polymer is a hydrogenated indene/methylstyrene/styrene copolymer and present in an amount of 2 to 15% by weight relative to the total weight of the composition.

* * * * *